United States Patent [19]
Palmer et al.

[11] Patent Number: 5,117,838
[45] Date of Patent: Jun. 2, 1992

[54] ROTATING GUIDEWIRE EXTENSION SYSTEM

[75] Inventors: Matthew A. Palmer, Miami; Fernando M. Viera, Hialeah, both of Fla.

[73] Assignee: Cordis Corporation, Miami Lakes, Fla.

[21] Appl. No.: 616,619

[22] Filed: Nov. 21, 1990

Related U.S. Application Data

[63] Continuation-in-part of Ser. No. 510,523, Apr. 18, 1990.

[51] Int. Cl.⁵ .............................................. A61B 5/00
[52] U.S. Cl. ...................................... 128/772; 128/657
[58] Field of Search ................. 128/657, 658, 772; 604/164, 283; 403/220, 221, 223, 229, 292

[56] References Cited

U.S. PATENT DOCUMENTS

| | | | |
|---|---|---|---|
| 161,508 | 3/1875 | Hare | 403/229 |
| 839,260 | 12/1906 | Benson | 403/229 |
| 2,077,309 | 4/1937 | Carlsson | 403/229 |
| 4,092,078 | 5/1978 | Klotz et al. | 403/221 |
| 4,827,941 | 5/1989 | Taylor et al. | 128/657 |
| 4,846,193 | 7/1989 | Tremulis et al. | 128/657 |
| 4,875,489 | 10/1989 | Messner et al. | 128/657 |
| 4,917,094 | 4/1990 | Lynch et al. | 128/657 |
| 4,922,923 | 5/1990 | Gambale et al. | 128/657 |
| 4,961,433 | 10/1990 | Christian | 128/772 |

*Primary Examiner*—Max Hindenburg
*Attorney, Agent, or Firm*—Henry W. Collins; Thomas R. Vigil

[57] ABSTRACT

The guidewire extension system includes an extension guidewire adapted to be releasably but firmly connected to the proximal end of an initial guidewire. The extension guidewire has a distal end and a proximal end, and the system further comprises a connecting assembly which is mounted at the distal end of the extension guidewire, which includes a coiled spring constructed and arranged to receive and grippingly engage and lock against a distal end of the initial guidewire, and which includes a swivel joint for minimizing, if not eliminating, twisting of the extension guidewire when disconnecting the extension guidewire from the initial guidewire.

16 Claims, 5 Drawing Sheets

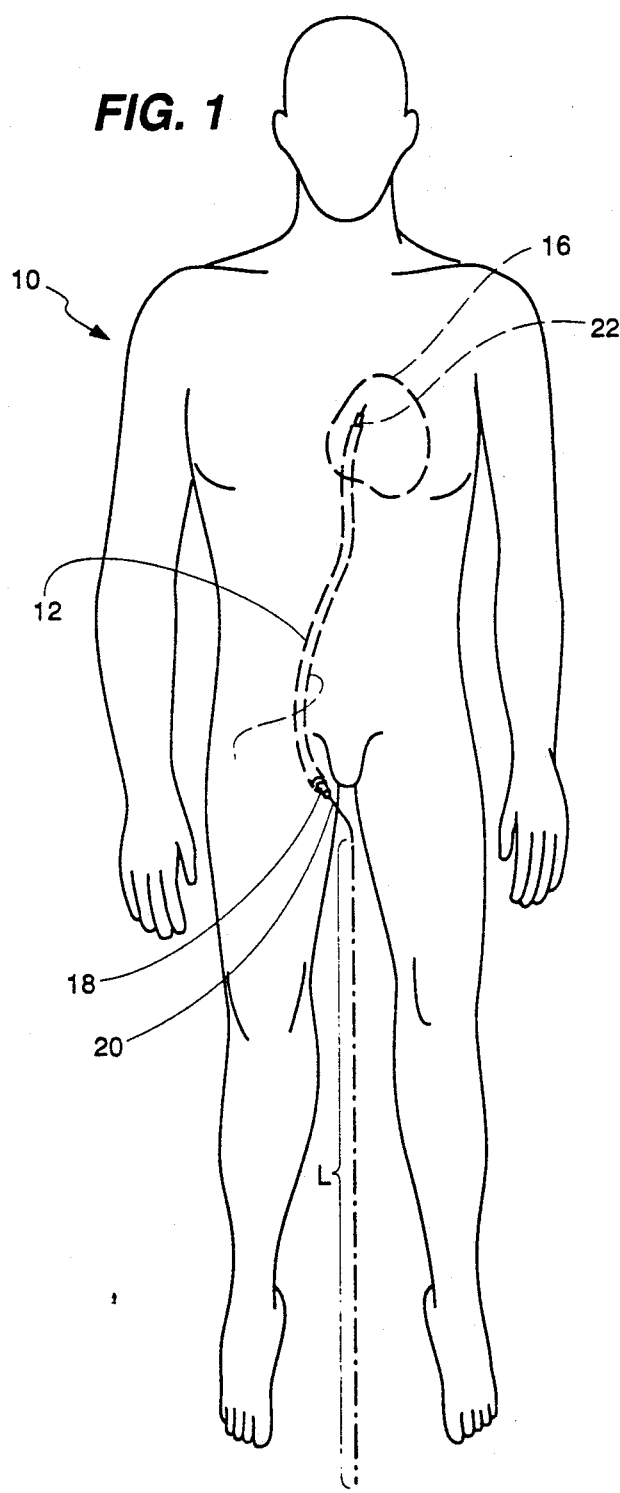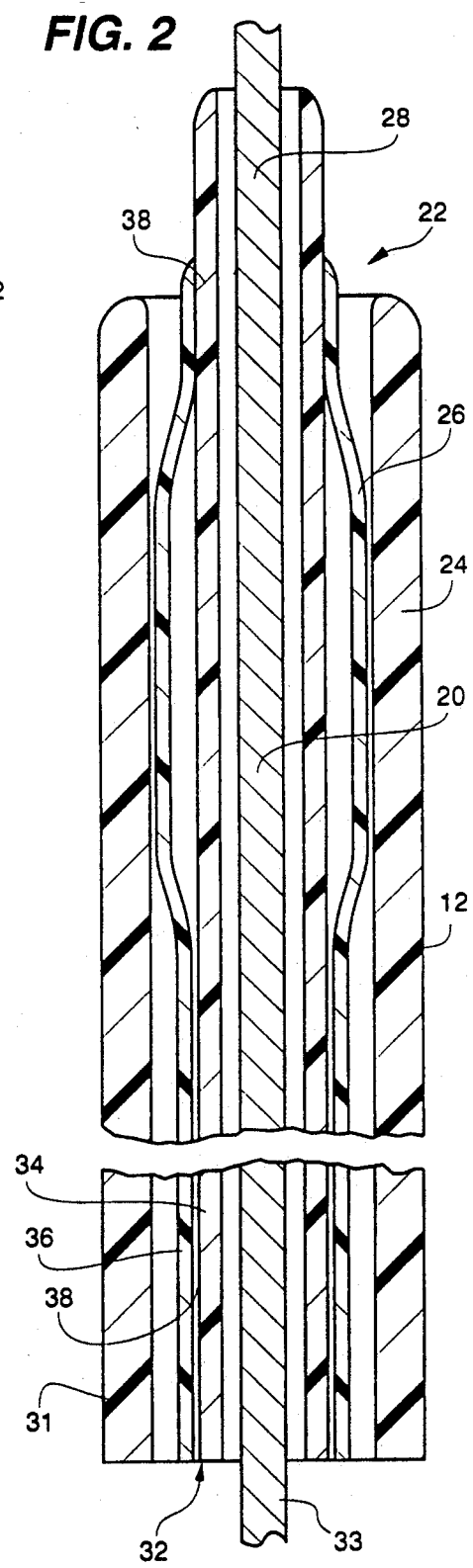

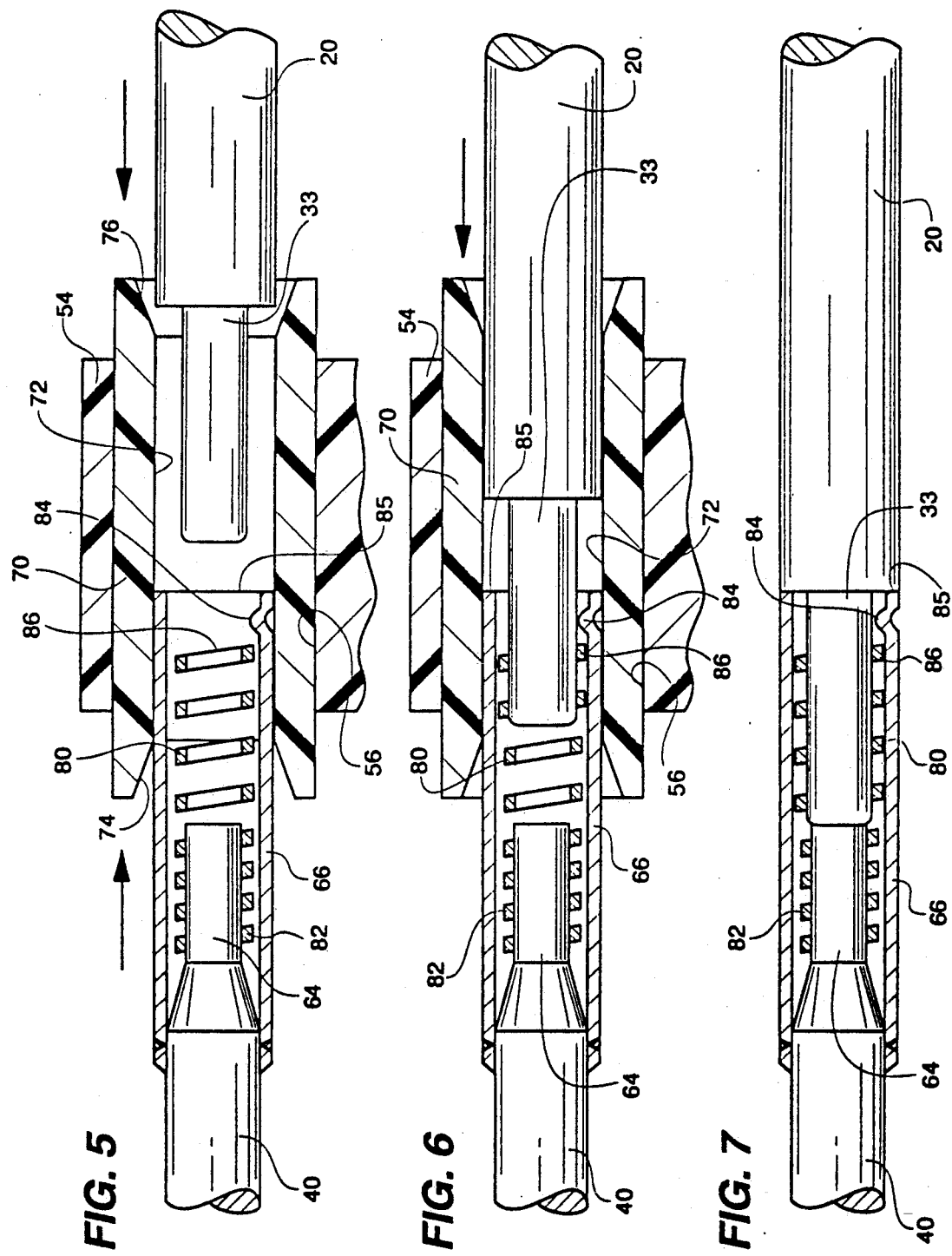

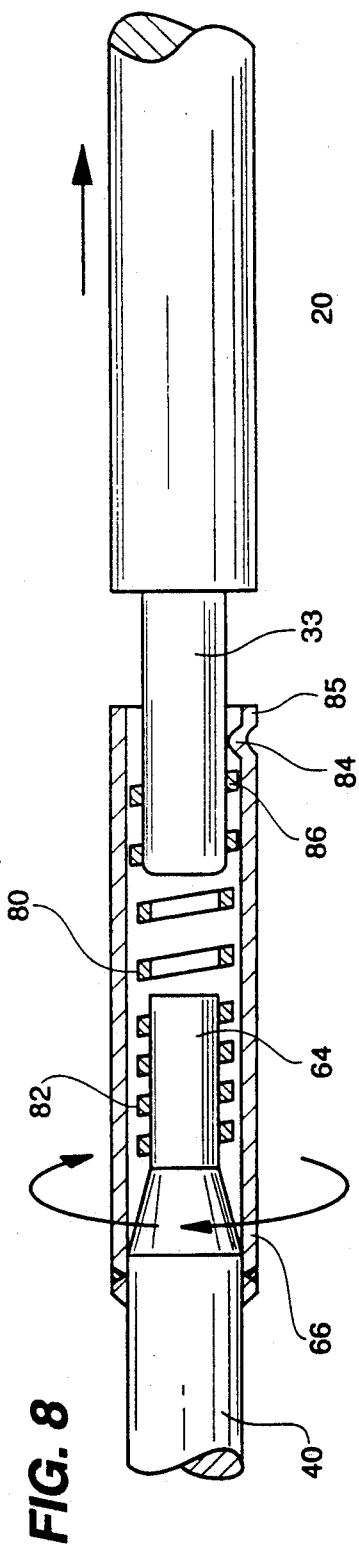

5,117,838

ROTATING GUIDEWIRE EXTENSION SYSTEM

CROSS-REFERENCE TO RELATED APPLICATION

This application is a Continuation-in-Part of U.S. application Ser. No. 07/510,523 filed Apr. 18, 1990 for: GUIDEWIRE EXTENSION SYSTEM.

BACKGROUND OF THE INVENTION

1. Field of the Invention

The present invention relates to a swivelling guidewire extension system including an extension guidewire having a connecting assembly at the distal end thereof for releasably and firmly connecting to a proximal end of an initially inserted PTCA guidewire having a dilatation balloon catheter positioned thereon and situated within a guiding catheter inserted into a femoral artery or carotid artery, for enabling the dilatation balloon catheter to be removed and replaced with another dilatation balloon catheter 2. Description of the related art including information disclosed under 37 CFR §§ 1.97-1.99

Heretofore, it has been proposed to provide an exchange guidewire which, after removal of a shorter initially inserted guidewire, is inserted through a dilatation balloon catheter situated in a guiding catheter inserted femoral artery for tho purpose of replacing the dilatation balloon catheter Since the procedure of utilizing an exchange guidewire is tedious, painstaking, time consuming and has some risk involved, it has also been proposed to utilize a guidewire extension for introducing a new dilatation catheter into a cardiovascular system.

For example, there is proposed in U.K. Patent Application No. 2 180 454 A guidewire system where the proximal end of an initially inserted guidewire is received in a sleeve which is also received over the distal end of an extension wire and the sleeve is crimped to fix the mating ends of the guidewire and extension wire together Also, an extendable guidewire system has been proposed in U.S. Pat. No. 4,827,941 wherein a small diameter proximal end portion of a primary or initial guidewire is frictionally received within a tubular member fixed to a distal end of a guidewire extension section.

Further, an extendable guidewire for introducing a dilatation catheter into a cardiovascular system has been proposed in U.S. Pat. No. 4,875,489 where the proximal end of a main guidewire has a tapered end portion which is received into a tubular member having a slit or slot therein which permits it to expand, the tubular member being received within an outer sleeve and fixed to a reduced in diameter distal end of a section of an auxiliary guidewire.

As will be described in greater detail hereinafter, the guidewire extension system of the present invention provides a simple connecting assembly including a coiled wire spring for quickly and firmly connecting (locking) the proximal end of an initially inserted guidewire to an extension guidewire and which permits quick and simple disengagement of the initially inserted guidewire from the connecting assembly while at the same time minimizing or eliminating twisting of the extension guidewire by providing a swivel connection of the extension guidewire to a tube of the connecting assembly.

SUMMARY OF THE INVENTION

A guidewire extension system comprising an extension guidewire adapted to be releasably but firmly connected to a proximal end of an initial guidewire. The extension guidewire has a distal end and a proximal end and the system further comprises a connecting assembly which is mounted at the distal end of the extension guidewire, which includes a coiled spring constructed and arranged to receive and grippingly engage and lock against the proximal end of the initial guidewire, and which includes a swivel joint for minimizing, if not eliminating, twisting of the extension guidewire when disconnecting the extension guidewire from the initial guidewire.

BRIEF DESCRIPTION OF THE DRAWINGS

FIG. 1 is a diagrammatic plan view of a patient undergoing catheterization for heart blood vessel angioplasty and shows a catheter inserted percutaneously into and through the femoral artery to the heart, the proximal ends of the catheter and initial guidewire protruding proximally, and shows an extension guidewire;

FIG. 2 is an enlarged longitudinal sectional view of the catheter and guidewire with portions broken away;

FIG. 5 is an enlarged longitudinal sectional view of the tool showing the small diameter tubing inserted in the tool and the proximal end of the guidewire positioned for insertion into the tool;

FIG. 6 is an enlarged, longitudinal sectional view of the tool showing the small diameter tubing inserted in the tool, similar to the view shown in FIG. 5, and shows the proximal end of the guidewire inserted into a small coiled spring situated within the small diameter tube and fixed to the distal end of the guidewire extension guideline;

FIG. 7 is an enlarged longitudinal sectional view of the small diameter tube with the proximal end of the initial guidewire received therein and within the coiled spring;

FIG. 8 is an enlarged, longitudinal sectional view of the tube with the small tubing received therein and with the proximal end of the initial guidewire being pulled and simultaneously rotated in a direction which causes expansion of the coiled spring to allow the proximal end of the initial guidewire to be withdrawn from the small diameter tube.

DESCRIPTION OF THE PREFERRED EMBODIMENTS

Figure 3:
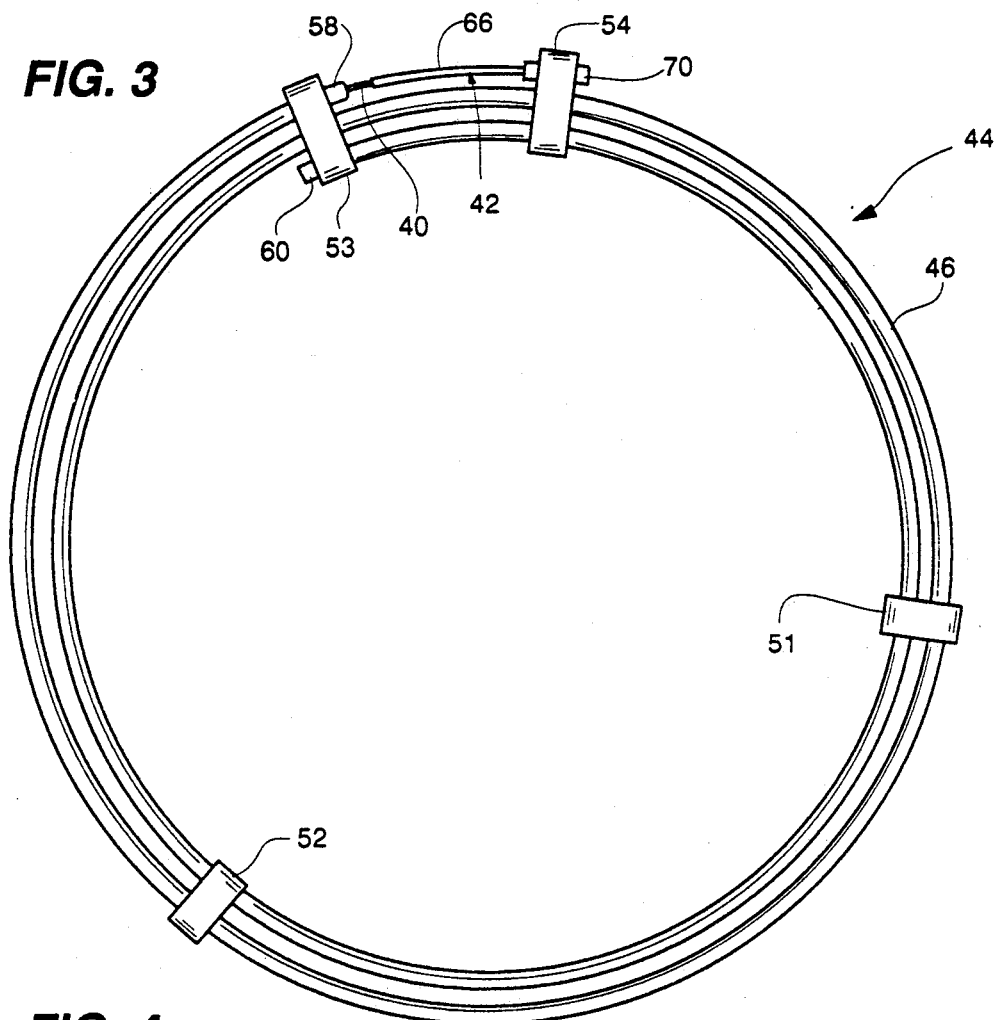
FIG. 3 is a plan view of a coiled plastic tube assembly mounting an extension guidewire constructed according to the teachings of the present invention.
Figure 4:
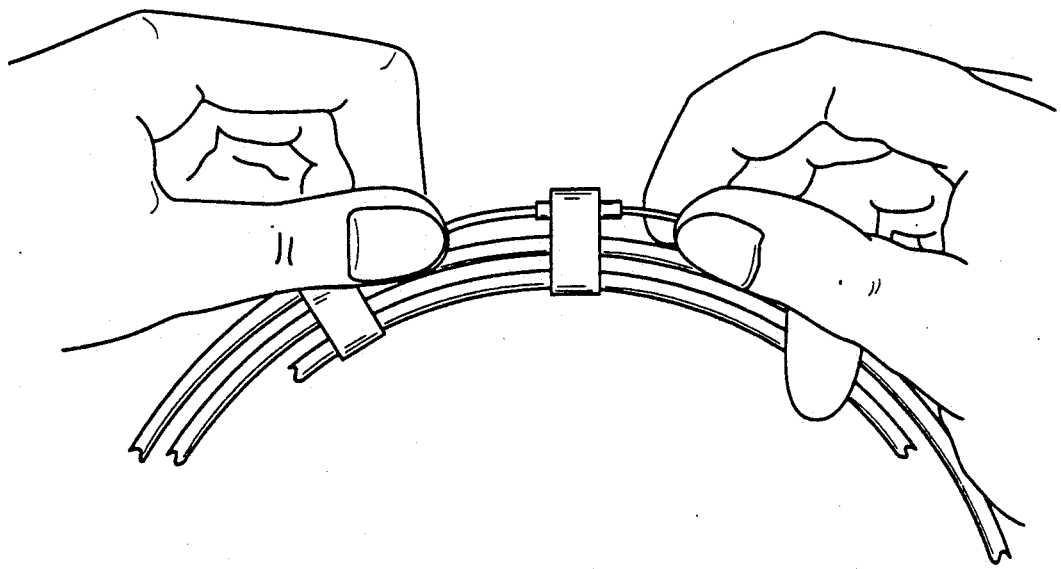
FIG. 4 is a fragmentary plan view of a portion of the coiled tube assembly shown in FIG. 1 and shows a small diameter tube fixed to the distal end of the extension guidewire inserted into a tool situated in an alignment tool holder mounted to the coiled tube assembly and a proximal end of the initial guidewire inserted into the tool for being guided into the small diameter tube.

Referring now to FIG. 1 there is illustrated therein a patient 10 undergoing catheterization for heart angioplasty. For this purpose a guiding catheter 12 had been previously inserted percutaneously into and through the femoral artery 14 into the heart 16. Then a balloon catheter 18 with an initial guidewire 20 therein is inserted through the guiding catheter 12 to place a distal end portion 22 of the balloon catheter 18 and guidewire 20 within the heart.

An enlarged view of a distal end portion 24 of the guiding catheter 12 having the distal end portion 22 of the balloon catheter 18 with a balloon formation 26, and a distal end 28 of the guidewire 20 therein is shown in FIG. 2. Also shown are the proximal ends 31, 32, 33 of the guiding catheter 12, the balloon catheter 18 and the guidewire 20, respectively. It will be understood that the proximal end 32 of the balloon catheter 18 is connected in a conventional manner to a source of dilatation fluid.

From FIG. 2 it will be seen that the balloon catheter 18 includes a main catheter portion 34 which is received over the initial guidewire, and a balloon catheter portion 36 which is received around and fixed to the main catheter portion 34 adjacent a distal end 38 of the main catheter portion 34. The balloon catheter portion 34 includes the balloon formation 26 in the distal end portion of the balloon catheter 18 as shown.

In use, the distal end portion 22 of the balloon catheter 18 and initial guidewire 20 are moved into an area of stenosis within a blood vessel. Then, a dilatation fluid is supplied through a annular space 38 between the balloon catheter portion 36 and the main catheter portion 34 to the balloon formation 26 for inflating or dilating same thereby to press the stenotic build-up outwardly against the walls of the blood vessel thereby to open the restricted passageway through the stenotic area. Once this has been achieved, the balloon catheter 18 initial guidewire 20 and guiding catheter 12 can be withdrawn or a stent can be implanted in the area of stenosis and then the balloon catheter 18 initial guidewire 20 and guiding catheter 12 are withdrawn.

Often the balloon catheter 18 chosen is the wrong size, the balloon 26 being too small or to large. When this occurs, it is necessary to remove the balloon catheter 18 and replace the same with a new balloon catheter. However, the length of the initial guidewire 20 is such that the whole assembly of balloon catheter 18 and guidewire 20 would have to be removed and replaced with a new balloon catheter and guidewire. This would be a tedious, painstaking and time consuming task, as well as unsafe, and it would be easier if the initial guidewire could be left in place with the initial balloon catheter 18 being removed and then replaced with a new balloon catheter. To enable the old guidewire to be utilized, techniques have been developed for using an exchange guidewire or an extendable guidewire which is capable of being attached and detached from the proximal end of the initially inserted guidewire 20.

It is desirable that the connection or attachment of an extension guidewire be simple and be easily detachable while maintaining a firm attachment or connection between the extension guidewire and the initially inserted guidewire 20.

An extension guidewire 40 and connecting assembly 42 for connecting to the proximal end 33 of the inserted guidewire 20, constructed according to the teachings of the present invention for achieving this function is shown in FIGS. 3-8.

As shown in FIG. 1, the extension guidewire 40 must have a sufficient length L so that the inserted balloon catheter 18 can be withdrawn over the initially inserted guidewire 20 and the extension guidewire 40 connected thereto and completely out of the guiding catheter 12 and then removed from the extension guidewire 40 so that a new balloon catheter then can be inserted over the extension guidewire 40 and then into the guiding catheter 12 over the initially inserted guidewire 20 to position the balloon 26 thereof in the area of stenosis to be treated.

Referring now to FIG. 3, there is illustrated therein a coiled plastic tube assembly 44 including a coiled plastic tube 46 which is held in a coiled position by four (4) holders 51-54 of the assembly the holders 51-54 have slots or holes 56 (FIG. 5) therethrough for receiving portions of the coiled tube 46. Two of the holders 51, 52 have two slots/holes 56 and two holders 53, 54 have three slots/holes 56. One of the holders 53 hold end portions 58, 60 of the coiled tube 46 with a distal end portion 62 of the extension guidewire 40 extending from the open upper or outer end 58 of the coiled tube 46 to and into one of the slots 56 in the holder 54 mounted on the coiled tube 46 a short distance from the holder 53.

According to the teachings of the present invention, a distal end 64 of the extension guidewire 40 is mounted in a small diameter tube 66, i.e. a tube having the diameter of a hypodermic needle, as shown in FIG. 5. The tube 66 forms part of the connecting assembly 42 mounted to the distal end 64 of the extension guidewire 40.

The tube 66 is received in an alignment tool 70 mounted in one of the slots 46 in the holder 54. The alignment tool 70 is cylindrical in structure and has a cylindrical throughbore 72 which flares or tapers outwardly at each end 74, 76 to facilitate insertion of the small diameter tube 66 in one end 74 and the proximal end 33 of the initial guidewire 20 at the other end 76.

As shown in FIGS. 5-8, inside the small diameter tube 66 of the connecting assembly 42 is an open pitch, flat wire coiled spring 80. Typically the coiled spring 80 has an internal diameter of approximately 0.008 inch and has an inner end 82 which is placed over the ground down distal end 64 of the extension guidewire 40 and welded thereto. The initial guidewire 20 typically has an outer diameter of approximately 0.013-0.014 inch and the proximal end 33 of the initial guidewire 20 is ground down to approximately 0.009 inch.

The tube 66 has a detent or dimple 84 punched therein adjacent an outer end 85 of the tube 66 which engages and prevents an outer end 86 of the spring 80 from being moved out of the tube 66 when the spring 80 is urged out of the tube 66 when the initial guidewire 20 is pulled while the connecting assembly 42 is held against movement.

Referring now to FIGS. 5, 6 and 7, the proximal end 33 of the initial guidewire 20 is inserted into the tool 70 and the proximal end 33 is urged toward the connecting assembly 42 until the proximal end 33 of the initial guidewire 20 engages or bottoms against the distal end 64 of the extension guidewire 40 within the coiled flat wire spring 80. Coils of the flat wire spring 80 then grip or lock against the proximal end 33 of the initial guidewire 40. The above described assembly establishes a secure joint between the distal end 64 of the extension guidewire 40 and the proximal end 33 of the initial guidewire 20.

The coiled tube 46 can then be moved away from this joint to effect removal of the extension guidewire 40 from the coiled tube 46.

Now the implanted "old" balloon catheter 18 can be removed over the extension guidewire 40 and a new balloon catheter can be inserted over the extension guidewire 40 and the initial guidewire 20 to place a new balloon in the stenotic area in a blood vessel.

The extension guidewire 40 and initial guidewire 20 assembly is very effective since, as the proximal end 33 of the initial guidewire 20 is inserted into the coils of the flat wire coiled spring 80, the coils of the coiled spring 80 are forced to uncoil slightly, i.e., move in a direction which establishes a slightly greater inner diameter of the coils, so that the coils can receive therein the outer diameter of the proximal end 33 of the initial guidewire 20. Then, an axial force pulling the proximal end 33 away from the coiled spring 80 causes the coils around the proximal end 33 to tend to move toward a smaller inner diameter and that tendency establishes a locking connection between the coils and the proximal end 33.

If the extension guidewire 40 is pulled, the coiled spring 80 tries to axially extend causing it to try to reduce its internal diameter and this greatly increases the locking force of the flat wire coiled spring 80 against the proximal end 33 of the initial guidewire 20.

Furthermore, as shown in FIG. 8, it is a simple matter to disengage the extension guidewire 40 from the initial guidewire 20. Disengagement is achieved simply by rotating the extension guidewire 40 to loosen the grip of the spring 80 against the proximal end 33 of the initial guidewire 20 while at the same time pulling the initial guidewire 20 or vice versa to pull the proximal end 33 thereof out of engagement with the coils of the flat wire coiled spring 80 and out of the small diameter tube 66. The detent 84 prevents the outer end 86 of the spring from being pulled out of the tube 66.

The extension guidewire 40 is a flexible 304 stainless steel wire coated with polymerized silicone. The extension guidewire 40 is 125 cm. long and has a diameter of approximately 0.013-0.014 inch. The tube 66 is made of 304 stainless steel and the spring 80 is made of a high tensile strength 304 stainless steel.

With the use of the spring 80 locking against the proximal end 33 of the initial guidewire 20 and the detent 84 blocking movement of the outer end 86 of the spring 80 out of the tube 66, a gripping force is established which would require at least a three pounds axial force to break the connection between the spring 80 and the proximal end 33 of the initial guidewire 20 while allowing the proximal end 33 and the spring 80 to "spin apart" freely. Note that as the spring 80 is pulled axially in a direction out of the tube the coils thereof are urged to a smaller diameter thereby to lock further against the proximal end 33 of the initial guidewire 20 when the initial guidewire 20 is pulled away from the tube 66.

Preferably, the tube 66 is colored a different color than the extension guidewire 40 to facilitate locating of the tube 66 by a medical practitioner.

Further it is to be understood that the position of the connecting assembly 42 including the tube 66 and the spring 80 can be reversed. That is to say, the connecting assembly 42 can be mounted on the proximal end 30 of the initial guidewire 20, and inserted in the alignment tool 70 to connect with the distal end 64 of the extension guidewire 40.

The coiled tube assembly 44 with extension guidewire 40 therein is packaged in a sterile pouch (not shown) and when used, the following steps are followed:

1. Open the sterile pouch slowly and remove the coiled dispensing tube 46 containing the extension guidewire 40;

2. Insert the proximal end 33 of the primary (initial) guidewire 20 into the alignment tool 70 and gently push the proximal end 33 of the primary or initial guidewire 20 until it is fully seated in the small diameter tube 66;

3. Carefully pull the extension guidewire 40 out of the coiled dispensing tube 46 and alignment tool 70 to prevent it from springing onto a non-sterile field and to prevent kinking of the extension guidewire 40.

CAUTION: Before use, flush all devices entering the vascular system with sterile, heparinized saline or similar isotonic solution.

4. Exchange the dilatation catheters 18 using standard PTCA procedures.

CAUTION: If strong resistance is met during manipulation, discontinue the procedure and determine the cause for the resistance before proceeding.

5. The extension guidewire 40 now can be disengaged from the primary or initial guidewire 20 if desired. This is achieved by holding the proximal end 33 of the primary or initial guidewire 20 while rotating the extension guidewire 40 in a direction so as to expand the spring thereby to loosen the spring, and at the same time gently pulling it backwards until it separates from the primary or initial guidewire 20.

It is to be noted that when using the extension guidewire system of the present invention described above, some twisting of the guidewire 40 may be incurred when rotating the connecting assembly 42 to disconnect the initial guidewire 20 from the connecting assembly 42.

Figure 9:
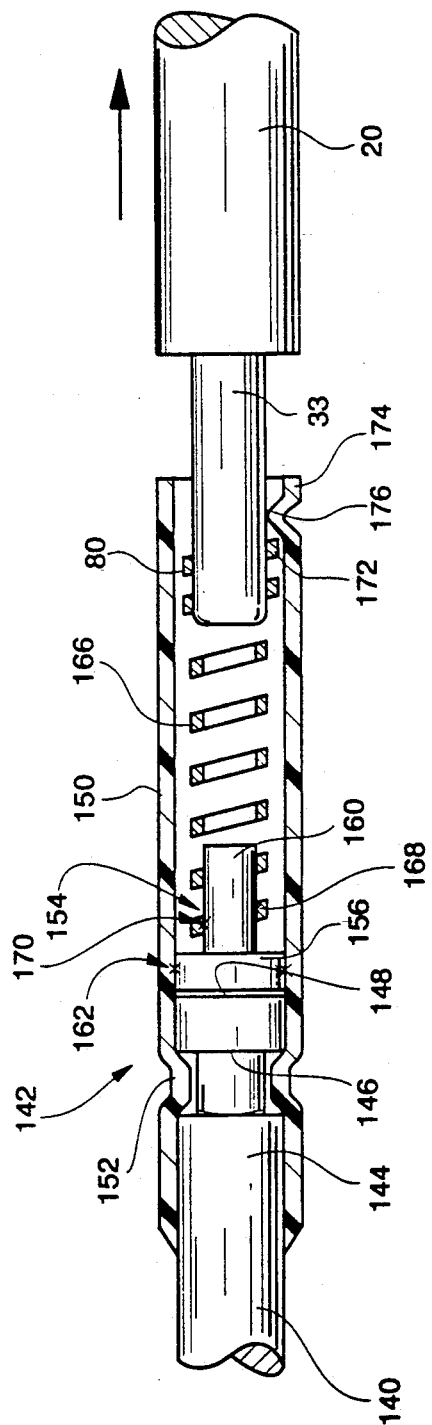
FIG. 9 is an enlarged, longitudinal sectional view of a modified tube having a swivel joint assembly at the proximal end of the tube.

To minimize, if not altogether eliminate, twisting of the guidewire extension 40 when disconnecting the extension guidewire 40 from the initial guidewire 20, a modified extension guidewire 140 and modified connecting assembly 142 can be provided as shown in FIG. 9.

Referring now in greater detail to FIG. 9, there is shown therein a distal end portion 144 of the extension guidewire 140. As shown, the distal end portion 144 has an annular groove 146 cut therein and spaced a short distance from an outer distal end 148 of the extension guidewire 140.

The connecting assembly 142 includes a small diameter tube 150 which is swaged at 152 to form an annular detent which is in registry with the annular groove 146. This construction provides a swivel connection of the extension guidewire 140 to the tube 150 with the annular groove 146 and the annular detent permitting relative rotational movement but not axial movement between the extension guidewire 140 and the tube 150.

As shown, the connecting assembly 142 further includes a step-down piece 154 which includes a disc shaped proximal portion 156 and a reduced-in-diameter distal rod-shaped portion 160. The proximal portion 156 is fixed, such as by weld 162, to the inside of the tube 150.

Then, as in the connecting assembly 142, a flat coiled spring 166 is provided having a proximal end 168 which is fixed, such as by weld 170, to the rod-shaped distal portion 160 of the step-down piece 154 on which it is received.

With this construction, the flat guidewire 166 is fixed to the step-down piece 154 and the step-down piece 154 is fixed to the tube 150 whereby the tube 150 can be rotated to rotate the coiled spring 166 relative to the reduced-in-diameter proximal end portion 33 of the initial guidewire 20.

The coiled spring 166 is identical to the coiled spring 80 of the coupling assembly 42 and has a distal end 172. Then, a distal end portion 174 of the tube 150 has a detent 176 formed therein in the same manner as the detent 84 for the purpose of retaining and holding the coiled spring 166 within the tube 150.

In this embodiment of the extension guidewire system, the connecting assembly 142 can swivel or is rotatable relative to the guidewire 140 so that the guidewire 140 does not have to be twisted when the tube 150 is rotated to cause the coiled flat wire spring 166 to disengage from its gripping engagement with the reduced-in-diameter proximal end 33 of the initial guidewire 20 which then can be pulled, as shown by the arrow in FIG. 9, from the connecting assembly 142 when disengaging the initial guidewire 20 from the extension guidewire 140.

The extendable guidewire system including the extendable guidewire 140 and connecting assembly 142 of the present invention has a number of advantages some of which have been described above and others of which are inherent in the system. Additionally, modifications can be made to the extension guidewire system without departing from the teachings of the present invention. Accordingly, the scope of the invention is only to be limited as necessitated by the accompanying claims.

We claim:

1. A guidewire extension system comprising: an extension guidewire adapted to be releasably but firmly connected to a proximal end of an initial or primary guidewire, said extension guidewire having a distal end and a proximal end, and a connecting assembly which is mounted at the distal end of said extension guidewire, which includes a coiled spring constructed and arranged to receive and grippingly engage and lock against a proximal end of the initial or primary guidewire, and which includes a small diameter tube having a proximal end and a distal end, said coiled spring being received in said tube, said distal end of said extension guidewire being received in said proximal end of said tube, and a rotatable connection between said distal end of said guidewire and said proximal end of said tube providing rotatable journaling of said extension guidewire to said tube for minimizing, if not eliminating, twisting of the extension guidewire when disconnecting the extension guidewire from the initial guidewire.

2. The guidewire extension system of claim 1 wherein said connecting assembly includes a step-down piece having a proximal portion and a reduced in cross-section distal portion, a small diameter tube received over said coiled spring and said step-down piece, said proximal portion of said step-down piece being fixed to said tube and said coiled spring being fixed to said distal portion of said step-down piece.

3. The guidewire extension system of claim 1 wherein said distal end of said extension guidewire has an annular groove therein and said proximal end of said tube has a swaged down annular detent which is in registry with said annular groove in a manner which permits relative rotational movement, but not axial movement between said extension guidewire and said tube.

4. The guidewire extension system of claim 1 wherein said coiled spring comprises an open pitch flat wire coiled spring having an internal diameter slightly less than the outer diameter of the proximal end of the initial guidewire so that, when the proximal end is urged toward said coiled spring, the coils of said coiled spring are caused to uncoil slightly to a slightly larger inner diameter to receive the proximal end therein.

5. The guidewire extension system of claim 1 wherein said tube has a detent punched therein adjacent the outer end of the tube for engaging and preventing the outer end of the coiled spring from being moved out of the tube when the proximal end of the initial guidewire is urged out of the tube.

6. The guidewire extension system of claim 1 wherein said connecting assembly includes a piece fixed in said tube, said coiled spring comprises an open pitch flat wire coiled spring having an internal diameter slightly less than the outer diameter of the proximal end of the initial guidewire so that, when the proximal end is urged toward the coils of said coiled spring, the coils of said coiled spring are caused to uncoil slightly to a slightly larger inner diameter to receive the proximal end therein, a proximal end of said coiled flat wire spring is fixed to said piece inside and fixed to said small diameter tube, and said tube which is received over said coiled spring has a detent punched therein adjacent the outer end of the tube for engaging and preventing the outer end of the coiled spring from being moved out of the tube when the proximal end of the initial guidewire is urged out of the tube, the coils of said coiled spring are urged to expand axially and to contract radially inwardly toward a smaller diameter when the proximal end is urged away from said tube, thereby causing the coils of said coiled spring to lock against the proximal end, and the locking force of said coils against the proximal end and the blocking force of said detent against a distal coil of said coiled spring, when the proximal end is pulled away from said tube, requires an axial pulling force of at least three pounds to pull the proximal end out of the connecting assembly.

7. The guidewire extension system of claim 1 wherein said tube is colored a different color than said extension guidewire to facilitate the locating of the tube.

8. The guidewire extension system of claim 1 further comprising an alignment tool which includes a body having a cylindrical passageway therethrough into one end of which the connecting assembly is inserted and into the other end of which is inserted the proximal end of the initial guidewire for being guided in an aligned manner into said connecting assembly.

9. The guidewire extension system of claim 8 wherein said cylindrical passageway in said alignment tool is flared or tapered radially outwardly at each end thereof to facilitate insertion of the connecting assembly in one end and the proximal end of the initial guidewire in the other end.

10. The guidewire extension system of claim 1 further comprising a coiled tube assembly including a coiled plastic tube assembly initially a coiled plastic dispensing tube in which the extension guidewire is received and stored in a sterile manner.

11. The guidewire extension system of claim 10 further comprising an alignment tool which includes a body having a cylindrical passageway therethrough into one end of which the connecting assembly is inserted and into the other end of which is inserted the proximal end of the initial guidewire for being guided in an aligned manner into said connecting assembly, said alignment tool being mounted to said coiled dispensing tube adjacent an outlet end of said coiled tube.

12. A guidewire extension system for coupling a distal end of an extension guidewire to a proximal end of an initial guidewire, said system comprising a rotatable connecting assembly mounted to one of: the distal end of the extension guidewire and the proximal end of the initial guidewire; and including a smaller diameter tube and a coiled spring fixed in said tube and constructed and arranged to receive the other of: the proximal end of the initial guidewire and the distal end of the extension guidewire.

13. A method for connecting an extension guidewire to an initial guidewire, said method comprising the steps of:

provide a length of extension guidewire;

providing a rotatable connecting assembly on one of: the distal end of the extension guidewire and the proximal end of the initial guidewire;

providing the rotatable connecting assembly with a small diameter tube and a coiled spring fixed in the tube and arranging same to receive and grippingly engage/lock against an end of a guidewire; and axially inserting into the connecting assembly and within the envelope of the coiled spring one of: the proximal end of the initial guidewire and the distal end of the extension guidewire; thereby to connect firmly the distal end of the extension guidewire to the proximal end of the initial guidewire.

14. The method of claim 13 including the further step of removing the extension guidewire by pulling the proximal end of the initial guidewire away from the coiled spring while simultaneously rotating the tube of the connecting assembly rotatably journaled on the distal end of the extension guidewire in a direction which loosens the grip of the spring against the end of the initial guidewire or the extension guidewire.

15. A method of replacing a dilatation balloon catheter previously inserted with an initial guidewire through a guiding catheter into a vascular system comprising the steps of:

performing the method steps defined in claim 13;

removing the initial dilatation balloon catheter over the extension guidewire; and inserting a new dilatation balloon catheter over the extension guidewire and the initial guidewire and positioning the balloon thereof at approximately the same location where the balloon of the initially inserted dilatation balloon catheter had been located.

16. The method of claim 15 including the further step of removing the extension guidewire by pulling the proximal end of the initial guidewire away from the coiled spring while simultaneously rotating the tube of the connecting assembly rotatably journaled on the distal end of the extension guidewire in a direction which loosens the grip of the spring against the end of the initial guidewire or the extension guidewire.

* * * * *

UNITED STATES PATENT AND TRADEMARK OFFICE
CERTIFICATE OF CORRECTION

PATENT NO. : 5,117,838

DATED : June 2, 1992

INVENTOR(S) : Donald A. McAfee et al.

It is certified that error appears in the above-identified patent and that said Letters Patent is hereby corrected as shown below:

Title page, item [57]:

Abstract, line 14, reads "adenosine agonist" and should read --adenosine antagonist--.

Column 12:

Claim 2, line 2, reads "receptor agonist" and should read --receptor antagonist--.

Claim 2, line 8, the phrase "preferably 5 to 6," should be deleted.

Claim 2, line 13, reads "can be" and should read --is--.

Claim 2, line 14, the phrase "for instance ethers and alcohols" should be deleted.

Claim 3, line 2, reads "receptor agonist" and should read --receptor antagonist--.

Claim 4, line 2, reads "receptor agonist" and should read --receptor antagonist--.

Claim 5, line 2, reads "receptor agonist" and should read --receptor antagonist--.

Claim 11, line 13, reads "A adenosine" and should read --$A_1$ adenosine--.

Claim 12, line 2, reads "receptor agonist" and should read --receptor antagonist--.

Claim 12, line 8, the phrase "preferably 5 to 6," should be deleted.

UNITED STATES PATENT AND TRADEMARK OFFICE
CERTIFICATE OF CORRECTION

PATENT NO. : 5,117,838
DATED : June 2, 1992
INVENTOR(S) : Donald A. McAfee et al.

It is certified that error appears in the above-identified patent and that said Letters Patent is hereby corrected as shown below:

Claim 12, line 13, reads "can be" and should read --is--.
Column 14:
Claim 12, line 14, the phrase "for instance ethers and alcohols" should be deleted.

Claim 13, line 2, reads "receptor agonist" and should read --receptor antagonist--.

Claim 14, line 2, reads "receptor agonist" and should read --receptor antagonist--.

Claim 15, line 2, reads "receptor agonist" and should read --receptor antagonist--.

Signed and Sealed this

Fifteenth Day of March, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,117,838
DATED : June 2, 1992
INVENTOR(S) : Palmer, et al

It is certified that error appears in the above-indentified patent and that said Letters Patent is hereby corrected as shown below:

Column 1, line 22 "catheter" should read --catheter.--
Column 1, line 29 "tho" should read --the--
Column 1, line 30 "catheter" should read --catheter.--
Column 1, line 42 "together" should read --together.--
Column 6, line 51 "annular detent 52" should read --annular detent 152.--

Signed and Sealed this

Fourth Day of October, 1994

Attest:

BRUCE LEHMAN

Attesting Officer

Commissioner of Patents and Trademarks